US009725103B2

(12) United States Patent
Weigel

(10) Patent No.: US 9,725,103 B2
(45) Date of Patent: Aug. 8, 2017

(54) METHOD AND ARRANGEMENT FOR DETERMINING THE OCCUPANCY OF A RAIL VEHICLE

(71) Applicant: SIEMENS AKTIENGESELLSCHAFT, Munich (DE)

(72) Inventor: Henning Weigel, Moers (DE)

(73) Assignee: Siemens Aktiengesellshaft, Munich (DE)

( * ) Notice: Subject to any disclaimer, the term of this patent is extended or adjusted under 35 U.S.C. 154(b) by 0 days.

(21) Appl. No.: 14/396,758

(22) PCT Filed: Apr. 22, 2013

(86) PCT No.: PCT/EP2013/058297
§ 371 (c)(1),
(2) Date: Oct. 24, 2014

(87) PCT Pub. No.: WO2013/160251
PCT Pub. Date: Oct. 31, 2013

(65) Prior Publication Data

US 2015/0126166 A1 May 7, 2015

(30) Foreign Application Priority Data

Apr. 25, 2012 (DE) ........................ 10 2012 206 815

(51) Int. Cl.
*C12Q 1/68* (2006.01)
*B61L 15/00* (2006.01)
*G08G 1/123* (2006.01)

(52) U.S. Cl.
CPC ....... *B61L 15/0072* (2013.01); *B61L 15/0027* (2013.01); *G08G 1/123* (2013.01)

(58) Field of Classification Search
CPC .. B61L 15/00; B61L 15/0027; B61L 15/0072; G08G 1/123
(Continued)

(56) References Cited

U.S. PATENT DOCUMENTS 7,469,827 B2 12/2008 Katragadda et al.
2008/0272906 A1 11/2008 Breed
(Continued)

FOREIGN PATENT DOCUMENTS

CN 201654868 U 11/2010
CN 102238584 A 11/2011
(Continued)

OTHER PUBLICATIONS

Zhang Ruiping, "A regional passenger flow guidance system design based on mobile communication network", Mobile Communications Issue 24, Dec. 31, 2010—English abstract.
(Continued)

*Primary Examiner* — Timothy Pham
(74) *Attorney, Agent, or Firm* — Laurence Greenberg; Werner Stemer; Ralph Locher

(57) ABSTRACT

A method determines the occupancy of a rail vehicle. In order to be able to carry out such a method particularly easily with sufficient accuracy, switched-on states of mobile phones which are present on the rail vehicle are determined by a detecting device, and the occupancy of the rail vehicle is determined by an evaluation unit from the detected switched-on states. An arrangement also determines the occupancy of the rail vehicle.

10 Claims, 2 Drawing Sheets

(58) Field of Classification Search
USPC .................................................... 455/414.1
See application file for complete search history.

(56) References Cited

U.S. PATENT DOCUMENTS

| | | | | |
|---|---|---|---|---|
| 2012/0259509 | A1* | 10/2012 | Wittorf .................. | G06Q 50/28 701/34.4 |
| 2013/0168503 | A1* | 7/2013 | Cooper ............... | B61L 15/0027 246/167 R |

FOREIGN PATENT DOCUMENTS

| | | | |
|---|---|---|---|
| DE | 19755891 | A1 | 6/1999 |
| DE | 102005048647 | A1 | 4/2007 |
| DE | 102009023131 | A1 | 9/2010 |
| EP | 0923256 | A2 | 6/1999 |
| EP | 0923256 | B1 | 4/2007 |
| SU | 834736 | A1 | 5/1981 |
| WO | 2007061734 | A2 | 5/2007 |

OTHER PUBLICATIONS

Verkehrslagedienst [Traffic Service], Wikipedia, English translation (part).
Intrain Repeater, Wikipedia, English translation (part).

* cited by examiner

METHOD AND ARRANGEMENT FOR DETERMINING THE OCCUPANCY OF A RAIL VEHICLE

BACKGROUND OF THE INVENTION

Field of the Invention

It is known that the occupancy of a rail vehicle is an important characteristic variable for the operation of a rail vehicle. For this reason, previously the pressure in the air springs has been measured in order to acquire this characteristic variable if such springs are present in the respective rail vehicle. The number of passengers has also been counted for this purpose.

BRIEF SUMMARY OF THE INVENTION

The invention relates to a method for determining the occupancy of a rail vehicle and has the object of proposing, in addition to or instead of the known methods specified at the beginning, a method which can be carried out with sufficient accuracy in a particularly easy way.

In order to achieve this object, in a method for determining the occupancy of a rail vehicle, according to the invention switched-on states of cell phones which are present on the rail vehicle are determined by means of a detection device, and the occupancy of the rail vehicle is determined from the detected switched-on states by means of an evaluation unit.

Although it is known from the Internet publication http://de.wikipedia.org/wiki/Verkehrslagedienst to acquire movement data by means of cell phones, the aim here is to monitor cell phones which are carried by persons in road vehicles in order to determine the traffic situation and permit traffic jams to be driven around.

A significant advantage of the method according to the invention is considered to be the fact that it does not require special sensors because the cell phones which are usually kept switched on by the passengers on board the rail vehicle are used as sensors in that their switched-on states are determined by the detection device. In this context, the accuracy in the determination of the occupancy is sufficient because the proportion of the total number of passengers in the rail vehicle who are carrying cell phones on their person can be determined statistically.

In the method according to the invention, the switched-on states can be determined in different ways. It is considered particularly advantageous, because of the low technical expenditure, if the switched-on states of the cell phones are determined by detecting the ready to receive signals of the switched-on cell phones. A "ready to receive signal" of a switched-on cell phone is understood to be a signal which is generated by the cell phone in what is referred to as its "idle mode". In the technical language, the "idle mode" or "passive mode" differs from what is referred to as the "dedicated mode" in that in the "idle mode" an active link from the cell phone to the cell phone network is not set up and a connection channel set up by the mobile radio network has not been seized by the cell phone.

A rapid and accurate detection process can be achieved in that the detection device is a detection device of the rail vehicle. The evaluation unit is preferably arranged in the rail vehicle.

In this embodiment of the method according to the invention, in particular during determination of the switched-on states of the cell phones by detection of the ready to receive signals of the switched-on mobile phones, it is particularly advantageous to use a repeater of the rail vehicle as a detection device. Said repeater is in fact present in any case on the rail vehicle and only has to be slightly added to in order to carry out the method according to the invention. A repeater is understood to be a device such as is described, for example, on the Internet at the address http://wikipedia.org/wiki/Intrain-Repeater.

In another advantageous variant of the method according to the invention, the switched-on states of the cell phones are used by detecting the electromagnetic radiation of the switched-on cell phones, and a receiver arrangement for the electromagnetic radiation of the switched-on cell phones is used as a detection device. In this context, the radiation is detected solely at the physical level without telecommunications evaluation.

In the method according to the invention, the electromagnetic radiation can be detected by means of detection devices which are of different designs. Because of the comparatively low expenditure on installation, it is considered advantageous if the electromagnetic radiation of switched-on cell phones which are present on the rail vehicle is detected in its entirety by means of a receiver arrangement which is composed of a single receiver unit.

The electromagnetic radiation of the switched-on cell phones can be determined with greater accuracy, but also with higher expenditure, if the electromagnetic radiation of switched-on cell phones which are present on the rail vehicle is detected by means of a receiver arrangement which has a plurality of receiver devices which are arranged distributed in the rail vehicle.

Particularly reliable results are supplied by the method according to the invention if the switched-on states of the cell phones are not only determined by detecting the ready to receive signals of the cell phones but also the electromagnetic radiation of the switched-on cell phones is determined simultaneously and additionally. The occupancy can then be determined relatively accurately with an evaluation unit of corresponding design.

The invention relates to an arrangement for determining the occupancy of a rail vehicle and has the object of, on the one hand, configuring the arrangement in a particularly easy and therefore cost-effective way and, on the other hand, implementing it in such a way that the occupancy of a rail vehicle can be determined with sufficient accuracy.

In order to achieve this object, the arrangement has according to the invention a detection device which determines the switched-on states of cell phones which are present on the rail vehicle, and connected downstream of the detection device is an evaluation unit which determines the occupancy of the rail vehicle from the detected switched-on states.

With such an arrangement which is embodied according to the invention it is appropriately possible to achieve the same advantages as have already been described above in relation to the method according to the invention.

A rapid and accurate detection process can be achieved by arranging the detection device in the rail vehicle. The evaluation unit is preferably arranged in the rail vehicle.

The detection device can be embodied in different ways here in respect of the arrangement according to the invention. It is advantageous if the detection device is a repeater of the rail vehicle which detects switched-on states of the cell phones as ready to receive signals of switched-on cell phones. A repeater is generally always present in a rail vehicle.

It can also be advantageous if the detection device is embodied as a receiver arrangement with a single receiver unit which detects the entirety of the electromagnetic radiation of the switched-on cell phones on the rail vehicle.

As a result, a simple design with sufficient accuracy can be achieved.

In the case of the arrangement according to the invention, the detection device can advantageously also have a plurality of receiver devices which are arranged distributed in the rail vehicle and which detect electromagnetic radiation on the rail vehicle of the switched-on cell phones on the rail vehicle, as a result of which the accuracy of the detection of the electromagnetic radiation is improved, but the expenditure is also increased.

As in the case of the method according to the invention, with an advantageous embodiment of the arrangement according to the invention it is also possible to achieve relatively high accuracy in the determination of the occupancy if the detection device is embodied in such a way that it not only detects the ready to receive signals of the cell phones but also has a receiver device which determines the electromagnetic radiation of the switched-on cell phones.

An exemplary embodiment of the arrangement according to the invention can be embodied in such a way that a receiver arrangement for detecting the electromagnetic radiation of switched-on cell phones is accommodated, in at least one car forming a rail vehicle, in particular in the passenger compartment of said car. This receiver arrangement can be composed of a single receiver unit or of a plurality of receiver devices. The receiver arrangement outputs an output signal which is a measure of the electromagnetic radiation picked up from the switched-on cell phones located in the car. An evaluation unit is connected, considered in terms of switching technology, downstream of the receiver arrangement and the output signal of the receiver arrangement is applied to the input side of said evaluation unit. In the evaluation unit, a characteristic variable which is a measure of the occupancy of the rail vehicle or of the car is formed with the output signal of the receiver arrangement. In this context, the evaluation unit takes into account, during the formation of the characteristic variable, how many passengers usually travel with a cell phone, by using statistical data collection methods.

In the case of a passenger train with a plurality of cars, apart from the receiver arrangement an evaluation unit can also be present in each car. Each evaluation unit can then send a message to a superordinate evaluation arrangement which is assigned to the entire passenger train, with the result that a train-related characteristic number for the occupancy is then acquired.

On the other hand, it is also possible, in the case of a passenger train, to transmit output signals of the receiver arrangements of the individual cars to a single central evaluation unit of the passenger train and acquire the characteristic number for the occupancy of the entire train there.

DESCRIPTION OF THE INVENTION

Figure 1:
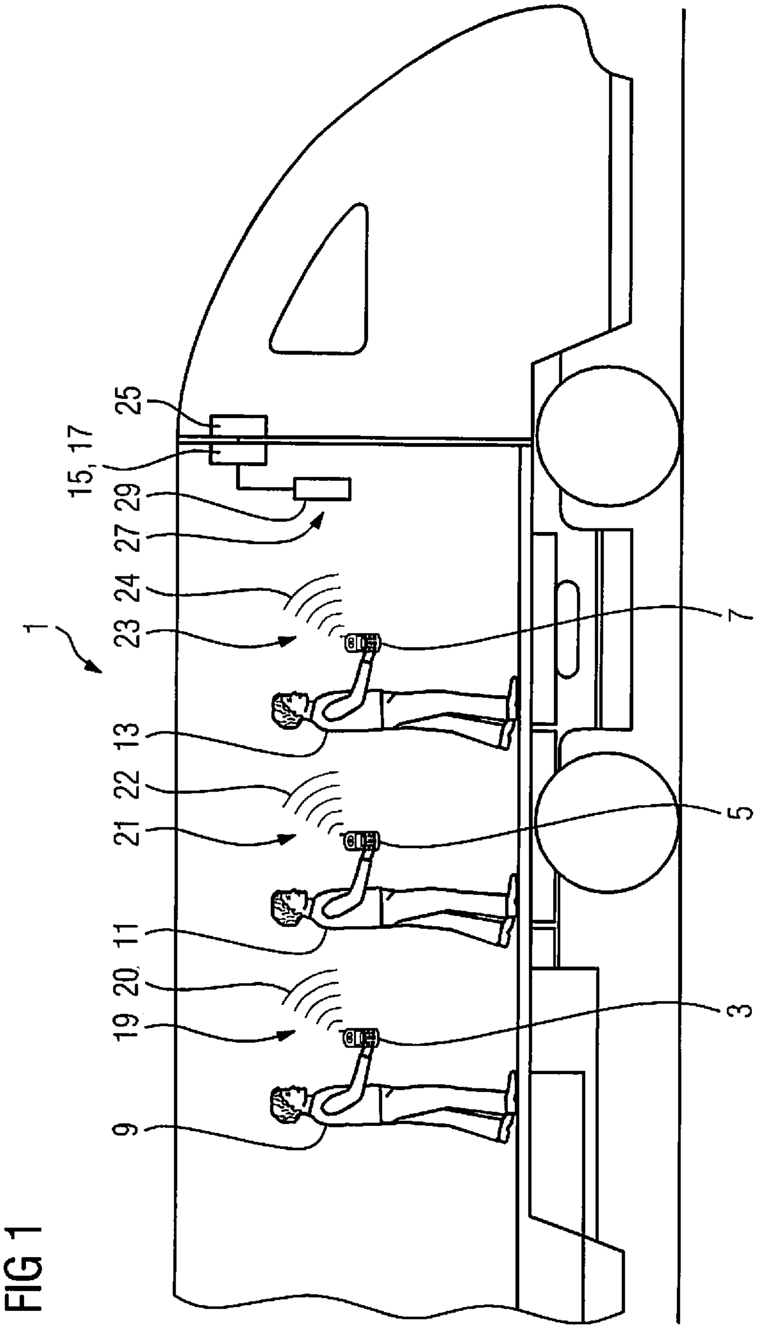
FIG. 1 is a diagrammatic, cross-sectional view of a rail vehicle carrying a configuration for determining an occupancy of the rail vehicle according to the invention.

Referring now to the figures of the drawings in detail and first, particularly to FIG. 1 thereof, there is shown a rail vehicle 1. Cell-phones 3, 5, 7 are carried by passengers 9, 11, 13 in the rail vehicle 1. The cell-phones 3, 5, 7 are in a switched-on state each. The switched-on states of the cell phones 3, 5, 7 are determined by a detection device 15. The detection device 15 is a detection device of the rail vehicle 1. The detection device 15 is a repeater 17.

The switched-on states of the cell phones 3, 5, 7 are determined by detecting electromagnetic radiations 19, 21, 23 of the switched-on cell phones 3, 5, 7. The detection device 15 has a receiver configuration 27 for detecting the electromagnetic radiations 19, 21, 23 of the switched-on cell phones 3, 5, 7. The electromagnetic radiations 19, 21, 23 of the switched-on cell phones 3, 5, 7 which are present on the rail vehicle 1 are detected in its entirety by the receiver configuration 27 which is composed of a single receiver unit 29.

The electromagnetic radiations 19, 21, 23 may comprise ready to receive signals 20, 22, 24 of the switched-on cell phones 3, 5, 7.

The occupancy of the rail vehicle 1 is determined from the detected switched-on states via an evaluation unit 25.

Figure 2:
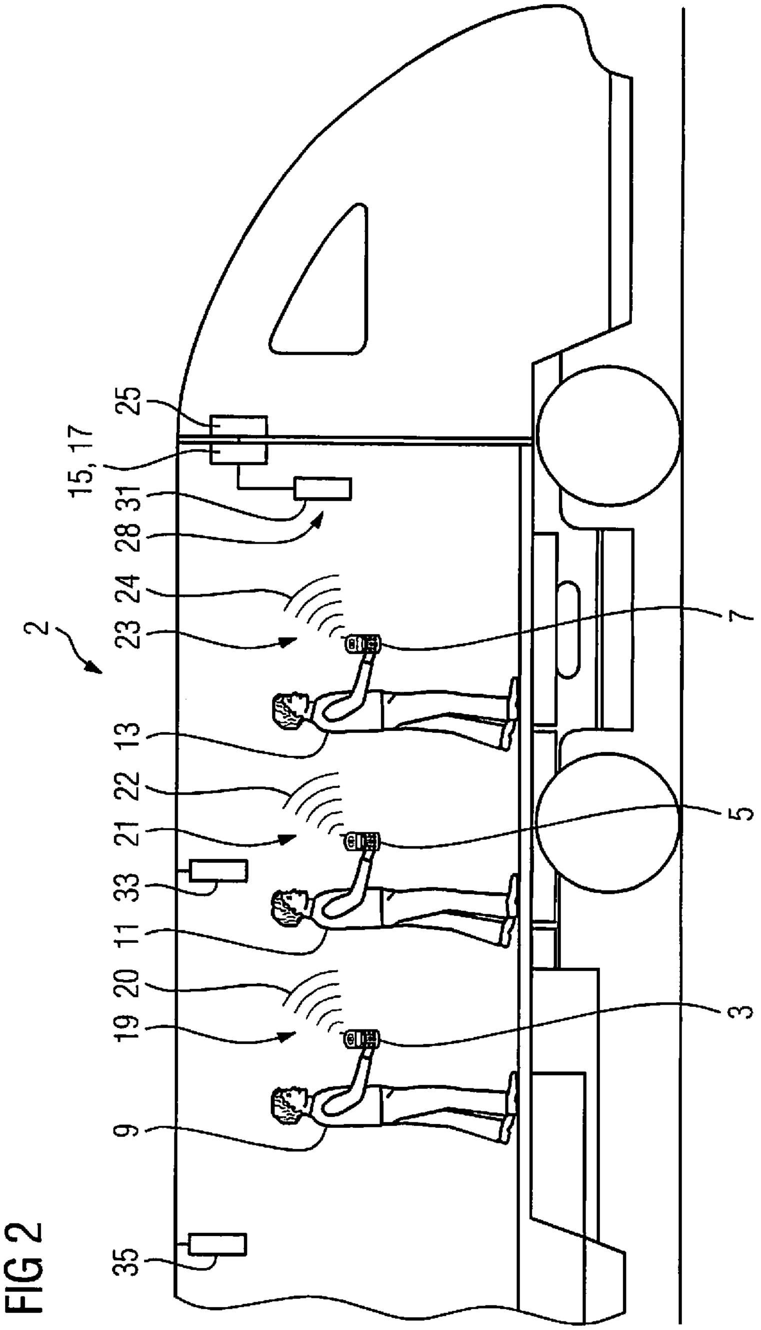
FIG. 2 is a cross-sectional view showing a further embodiment of the configuration for determining the occupancy of the rail vehicle.

FIG. 2 illustrates a rail vehicle 2 similar to the rail vehicle 1 illustrated in FIG. 1. The same and similar elements are referred to as by the same reference numerals. In FIG. 2 a receiver configuration 28 is illustrated which has a plurality of receiver devices 31, 33, 35 disposed in the rail vehicle 2.

The invention claimed is:

1. A method for determining an occupancy of a rail vehicle, which comprises the steps of:

determining switched-on states of cell phones present on the rail vehicle by a detection device, the detection device being a pre-existing detection device on the rail vehicle; and determining the occupancy of the rail vehicle from detected switched-on states via an evaluation unit, wherein the occupancy is a determination of a number of passengers on the rail vehicle and the number of passengers on the rail vehicle is equal to a number of the switched-on states of the cell phones plus a statistical variable based on how many passengers usually travel with a cell phone.

2. The method according to claim 1, which further comprises determining the switched-on states of the cell phones by detecting ready to receive signals of switched-on cell phones.

3. The method according to claim 1, which further comprises providing a repeater of the rail vehicle as the detection device.

4. The method according to claim 1, which further comprises:

determining the switched-on states of the cell phones by detecting electromagnetic radiation of switched-on cell phones; and providing the detection device with a receiver configuration for detecting the electromagnetic radiation of the switched-on cell phones.

5. The method according to claim 4, which further comprises detecting the electromagnetic radiation of the switched-on cell phones which are present on the rail vehicle in its entirety by means of the receiver configuration which is composed of a single receiver unit.

6. The method according to claim 4, which further comprises detecting the electromagnetic radiation of the switched-on cell phones which are present on the rail vehicle by means of the receiver configuration which has a plurality of receiver devices disposed distributed in the rail vehicle.

7. A configuration for determining an occupancy of a rail vehicle, the configuration comprising:

a detection device for determining switched-on states of cell phones present on the rail vehicle, wherein said detection device is disposed in the rail vehicle; and an evaluation device connected downstream of said detection device, said evaluation unit determining the occupancy of the rail vehicle from detected switched-on states, wherein the occupancy is a determination of a number of passengers on the rail vehicle and the number of passengers on the rail vehicle is equal to a number of the switched-on states of the cell phones plus a statistical variable based on how many passengers usually travel with a cell phone.

8. The configuration according to claim 7, wherein said detection device is a repeater of the rail vehicle which detects ready to receive signals of switched-on cell phones as the switched-on states of the cell phones.

9. The configuration according to claim 7, wherein said detection device contains a receiver configuration with a single receiver unit which detects electromagnetic radiation of switched-on cell phones on the rail vehicle.

10. The configuration according to claim 7, wherein said detection device has a plurality of receiver devices disposed distributed in the rail vehicle, said detection device detects electromagnetic radiation of switched-on cell phones on the rail vehicle.

* * * * *